United States Patent [19]

Westcott et al.

[11] 4,187,170

[45] Feb. 5, 1980

[54] MAGNETIC TECHNIQUES FOR SEPARATING NON-MAGNETIC MATERIALS

[75] Inventors: Vernon C. Westcott, Lincoln; John P. Bowen, South Hamilton, both of Mass.

[73] Assignee: Foxboro/Trans-Sonics, Inc., Burlington, Mass.

[21] Appl. No.: 870,206

[22] Filed: Jan. 17, 1978

Related U.S. Application Data

[63] Continuation-in-part of Ser. No. 762,981, Jan. 27, 1977, abandoned.

[51] Int. Cl.$^2$ .......................... B03B 1/00; B03C 1/00
[52] U.S. Cl. ........................................... 209/1; 209/8; 209/39; 209/214; 210/222
[58] Field of Search .................. 209/1, 4, 8, 9, 39, 209/212, 214; 210/222; 252/62.52, 62.56; 423/80, 151, 152

[56] References Cited

U.S. PATENT DOCUMENTS

| | | | |
|---|---|---|---|
| 861,782 | 7/1907 | Wait | 209/8 |
| 2,398,725 | 4/1946 | Schutte | 209/214 X |
| 3,483,969 | 12/1969 | Rosensweig | 209/1 |
| 3,843,540 | 10/1974 | Reimers et al. | 252/62.52 |
| 3,926,789 | 12/1975 | Shubert | 209/214 X |
| 3,929,627 | 12/1975 | Frangiskos et al. | 209/214 X |
| 3,970,518 | 7/1976 | Giaever | 210/222 X |
| 4,018,886 | 4/1977 | Giaever | 210/222 X |

OTHER PUBLICATIONS

West et al., "Handbook of Chemistry and Physics–47th edition", The Chemical Rubber Co., Cleveland, Ohio, 1966, pp. E-103 to E-108.

Primary Examiner—Arnold Turk
Attorney, Agent, or Firm—Parmelee, Johnson, Bollinger & Bramblett

[57] ABSTRACT

A process for magnetically separating non-magnetic material from a mixture by combining the mixture with a magnetizing solution containing the salt of a magnetic element. The magnetic atoms attach to available sites on the molecules of the non-magnetic material so as to develop in that material a positive susceptibility. Thus the material is responsive to the influence of a magnetic field to move the material to a region where it can be analyzed or recovered. Materials with low positive or negative susceptibilities are separated by suspending them in a magnetic salt solution which when subjected to the attraction of a magnetic field develops a differential buoyancy force, pushing the diamagnetic or weak paramagnetic material strongly away from the magnet. Disclosed are solutions of ferric chloride, manganese chloride, erbium chloride, dysprosium chloride, terbium chloride, and holmium chloride.

16 Claims, No Drawings

MAGNETIC TECHNIQUES FOR SEPARATING NON-MAGNETIC MATERIALS

CROSS-REFERENCE TO RELATED APPLICATION

This application is a continuation-in-part of parent application Ser. No. 762,981, filed by Vernon C. Westcott and John P. Bowen on Jan. 27, 1977, and now abandoned.

BACKGROUND OF THE INVENTION

1. Field of the Invention

This invention relates to the separation of materials by magnetic techniques. More particularly, this invention relates to the separation, or precipitation, of materials having very low positive or negative magnetic susceptibility. In one important aspect, this invention relates to the magnetic precipitation of diamagnetic materials, such as biological materials, human bone particles, and so forth.

2. Description of the Prior Art

The use of magnetic techniques for separating ferromagnetic materials from background substances has been known for quite some time. Recent refinements of such techniques have made it possible to precipitate hyperfine ferromagnetic wear particles from a lubricant sample taken from a machine, such as a diesel engine, and to determine the wear condition of the machine by optical analysis of such particles. A detailed description of apparatus and procedures for performing such precipitation and analysis is set forth in U.S. Pat. No. 4,047,814, issued on Sept. 13, 1977 to Veron C. Westcott.

In accordance with that prior disclosure, a lubricant sample is caused to flow along a shallow channel in a nearly horizontal glass substrate positioned over a magnet the air-gap of which is aligned with the longitudinal axis of the substrate. The magnet develops in the vicinity of the substrate, along the lubricant flow path, a magnetic field having a very high gradient perpendicular to the substrate surface. Ferromagnetic wear particles are drawn by magnetic force down from the lubricant liquid so as to precipitate onto the substrate surface.

In carrying out this procedure with ferromagnetic wear particles, the larger particles are precipitated first, and the smaller particles are precipitated further along the flow path. Analysis of the relative proportions of large and small size wear particles provides significant information about the state of wear of the machine from which the lubricant sample was taken. Similar techniques can be used to precipitate non-magnetic particles which wear against a ferrous metal such as steel, since the ferrous metal smears on or becomes embedded in the non-magnetic material which thus becomes effectively magnetic.

There are many occasions when it is desired to separate essentially non-magnetic particles which have not worn against a ferrous metal. Some of these materials are diamagnetic (popularly considered non-magnetic) and are weakly repelled by a magnetic field. Included in such materials of interest are wear particles from human joints, microscopic organisms, wear particles from plastic against plastic, ceramics, etc. It also is desired to precipitate weakly paramagnetic materials, such as aluminum, which are attracted towards an increasing magnetic field but with such a small force that the materials are usually considered non-magnetic.

Accordingly, it is an object of this invention to provide improved techniques for separating or precipitating by magnetic means materials which are essentially non-magnetic. A more specific object of the invention is to provide techniques for separating diamagnetic materials from various background substances. Other objects, aspects and advantages of the invention will in part be pointed out in, and in part apparent from, the following description of preferred embodiments of the invention.

In the following description, the term magnetic susceptibility is used in the usual sense, as the ratio of the intensity of magnetization produced in a substance to the magnetizing force or intensity of field to which it is subjected. Materials exhibit a wide range f susceptibilities.

A technique is described for imparting to some materials a relatively high positive susceptibilitiy. Materials that respond by developing the high magnetic susceptibilities are defined as susceptic materials.

SUMMARY OF THE INVENTION

In accordance with this invention, materials which are essentially non-magnetic are made to respond selectively to a magnetic field by immersing or suspending the material in a solution containing certain magnetic salts such as described below. Suspension in such salt solutions can produce one of two results, depending upon the relationship of the solution components with respect to the material to be precipitated. One of these results is that the suspended non-magnetic material develops a relatively high susceptibility so that, when the solution with the sample material is caused to flow along a substrate positioned over the air-gap of a magnet (as described in the above-identified U.S. Pat. No. 4,047,814), the suspended material is pulled down towards the substrate. Alternatively, in other cases, non-susceptic material (especially diamagnetic materials) will be pushed laterally away from the air-gap of the magnet so as to precipitate along the barrier layer defining the side walls of the substrate channel, remote from the longitudinal axis of center-line of the substrate. This latter result is the consequence of a differential force developed by the components of the salt solution being magnetically attracted towards the gap more strongly than the non-magntic material, thereby tending to repel the non-magnetic material, somewhat as a cork rises buoyantly to the surface of water.

Magnetic salt solutions which have been found to be especially effective for the above purposes are ferric chloride ($FeCl_3$) and manganese chloride ($MnCl_2$) dissolved in water or alcohol.

DESCRIPTION OF PREFERRED EMBODIMENTS

One important aspect of the present invention is based on the concept that a positive magnetic susceptibility can be imparted to essentially non-magnetic materials by suspending the materials in a solution containing a dissolved salt of a magnetic element. In particular, it has been discovered that such non-magnetic material can in some cases be made sufficiently magnetic to be precipitated by use of the techniques detailed in the above-mentioned U.S. Pat. No. 4,047,814. That is, the susceptic particles can be drawn down from a flowing carrier solution onto the surface of a substrate positioned in a magnetic field which extends along the longitudinal axis of the substrate.

As one specific example, it has been found that the salt ferric chloride when dissolved in water and added to an aqueous solution containing suspended organic matter such as algae, or particles of animal bone, or cartilage, will make the suspended material sufficiently magnetic so that it can be precipitated. An effective such solution was made by adding 3 g of $FeCl_3$ to 100 cc of $H_2O$. This solution then was mixed with an aqueous sample fluid containing the non-magnetic particles, in a ratio of two to one by volume, making a composite sample solution which was caused to flow along a substrate for magnetic precipitation of the particles. Another solution which rendered the non-magnetic particles magnetic was made by adding 3 g of $MnCl_2$ to 100 cc of $H_2O$, and again mixing the solution with an aqueous sample fluid in a two to one ratio.

As further specific examples, excellent results also have been achieved with each of the following four rare-earth salt solutions: erbium chloride ($ErCl_3$); dysprosium chloride ($DyCl_3$); terbium chloride ($TbCl_3$); and holmium chloride ($HoCl_3$). In each case, a room-temperature saturated solution of the salt, 5 cc in volume and free of crystals, was added to a 2 cc sample of bone meal slurry, and the resulting mixture was caused to flow along a substrate so as to effect magnetic precipitation of the bone meal particles on the substrate.

In using this technique, the susceptic particles precipitate along the center line of the substrate, within the pole pieces defining the magnetic air-gap, somewhat as in the case of ferromagnetic particles as described in U.S. Pat. No. 4,047,814. There are however some differences in the format of the precipitate. For example, the particles do not form string-like patterns commonly found with ferromagnetic particles.

It appears that in carrying out this process, magnetic atoms or complexes containing such atoms attach to available sites on the molecules of the non-magnetic particles. Experiments have indicated that this attachment phenomenon can be sufficient to cause the particulate material to have a higher positive susceptibility than the solution in which it is suspended. Different magnetic atoms or complexes are taken up in differing amounts, depending upon the material to be precipitated. By adjusting the salt concentration it becomes possible to select specific kinds of materials to be precipitated from various background substances, i.e. by selectively imparting a positive magnetic susceptibility to the desired material.

Experiments also have indicated that certain substances are more susceptic than others. For example, human bone appears to sequester magnetic ions readily and become magnetic even with dilute solutions. Other materials such as polyethylene resist ready attachment of the magnetic ions, and a high concentration of ions can be required to develop a suitably high susceptibility of the particles to be precipitated. In some cases, the ions may diffuse through the particles of interest.

Nonparticulate matter may also be made magnetic by such solutions. For example, we have found that glycoproteins from the synovial fluid drawn from human joints can be made magnetic when the fluid is mixed with the solution described. The same principles are applicable to small biological systems such as bacteria and viruses.

Materials have been made magnetic in nonaqueous as well as aqueous solutions by these techniques. This has been accomplished by the use of a transition fluid which permits solution of the magnetic salts in order that they may be introduced into a nonpolar sample. For example, a transition fluid has been formed of a non-polar solvent mixed with polar solvents and minor amounts of water. The fluid used consisted of 50% by volume of toluene, 25% acetone, 20% isopropyl alcohol, and 5% water. The magnetic salt was first dissolved in the transition fluid in sufficient amount to produce a saturated solution. A one cc sample of oil to be analyzed was separately combined with ten cc of transitional fluid, and the resulting solution added to the saturated salt solution in a ratio by volume, of one to five of the salt solution, to produce a composite sample solution suitable for analysis.

The magnetic action of the salt used in preparing the magnetizing solution can be selective as to the molecular species to which it attaches. In general, the shape, size and electronic structure of the magnetic atom may be expected to determine how readily it will attach to available sites on the molecules of the material to be precipitated. By selecting a particular atom, or complex containing the atom, individual components of the sample may be made to have more or less magnetic susceptibility, thus making possible, for example, differential precipitation effects, such as precipitating certain components and not precipitating others or precipitating one component in an early part of a sample fluid flow path, and other components in a later part of the path. Indications also have been found that the pH of the composite solution plays a part in determining the number of magnetic atoms or ions which will be attached to the material of interest.

Using the techniques described above, a number of different kinds of essentially non-magnetic materials have been precipitated, including bone and cartilage particles, particles of human synovia, elastomeric gasket material, polyethylene, polymethyl methacrylate, and starch.

The procedures described immediately above provide a technique for making magnetic certain materials which are effectively non-magnetic before treatment, so that those materials may be attracted by a magnetic field and separated from a background substance. However, there are materials which do not form attachments readily (or at all) with magnetic atoms or complexes as a consequence of their individual physical or chemical properties. For example, starch particles placed in an aqueous solution of the type described above remain diamagnetic. Since the negative susceptibility is only a few parts per million the direct repulsion force by the magnetic field is extremely small.

However, the fluid itself has a positive magnetic susceptibility so that it is attached towards the magnetic field. The resulting pressure gradient in the fluid generates a buoyancy force tending to push the particles away from the magnet. The magnet attracts the fluid, and the non-magnetic particles are forced back away from the increasing field. The net force on the particle is proportional to the difference in susceptibility of the fluid and the particles. Consequently particles with weak positive or with negative susceptibility are driven out of the magnetic field.

This result can be achieved by suspending the non-magnetic particles in a solution containing a dissolved salt of a magnetic element. Solutions of ferric chloride in water and manganese chloride in water have been used. If a solution containing the magnetic element and certain non-magnetic particles to be precipitated is caused to flow over a substrate in the presence of a strong magnetic field (as described in the above-identified U.S. Pat. No. 4,047,814), it has been found that the particles are deposited at the barrier layers defining the side walls of the substrate channel. That is, the particles are pushed laterally away from the longitudinal center line of the substrate, i.e. as far as possible away from the most intense and highest-gradient region of the field. The intensity of the repelling force is proportional to the difference in susceptibility of the solution and particle, the magnetic field gradient, and the magnetic field intensity.

These relationships may be expressed by the equation $$F \propto VH \, Grad \, (b_l - b_m)$$

$b_l$ = magnetic susceptibility of the liquid
$b_m$ = magnetic susceptibility of the material
Grad H = magnetic field gradient
H = external magnetic field intensity
V = volume of the particles
F = force on the particle The direction of the force is parallel with the field gradient and is away from the field if $b_l$ is larger than $b_m$.

Since virtually all of the magnetic force is generated by the attraction of the magnetic salt solution, the force disappears if the solution is washed away. Thus, if that step is followed by a wash that does not contain the salt, the particles of interest also will tend to wash away. On the other hand, if the flow of the magnetic salt solution is simply stopped and the liquid allowed to dry, the salts will crystallize on the substrate surface and obscure the particles of interest.

It has been found that such crystallization can be suppressed by employing a magnetic element solution that contains an additive agent adapted to suppress crystallization on drying, and which fixes the particles of interest in position. One such agent is photographic gelatin. When used in solution with manganese chloride, stoppage of flow along the substrate causes the solution to harden into a dry glass-like coating in which the particles are embedded. Manganese chloride is superior to ferric chloride because it is colorless in solution and the resulting film is water clear. A solution found to give good results is formed of 100 cc of $H_2O$, 1.5 g of $MnCl_2$ and 3.5 g of photographic gelatin. Four cc of such a solution was added to two cc of a sample fluid containing diamagnetic particles to be precipitated, and good separation was effected.

Although the above description showed how the invention can be used with the magnetic separation procedures as decribed in the above-mentioned U.S. Pat. No. 4,047,814, the present invention is not limited in its applicability to such separation techniques but is more generally applicable as will be apparent to those of skill in this art. Also, although specific preferred magnetic salt solutions have been set forth herein, it will be understood that other solutions can be effective in particular applications, depending upon various factors such as discussed hereinabove; for example, solutions of metallo-organic complexes can serve the same function.

We claim:

1. A process for separating a material of interest from a background substance by exposing a mixture thereof to a magnetic field, and wherein said material of interest is essentially non-magnetic and thus by itself not sufficiently responsive to the magnetic field to effect separation from said background substance, the method comprising the steps of:
combining said material with a solution of magnetic atoms to form a composite sample solution; and
transporting said composite sample solution through a magnetic field to develop a force on said material through magnetic influence on the atoms of said solution, said force serving to move said material to a region where it is recoverable from said background substance.

2. The method of claim 1, wherein said material is combined with an aqueous solution of a salt of the magnetic to form said composite sample solution atoms.

3. The method of claim 2, wherein said salt solution is ferric chloride.

4. The method of claim 2, wherein said salt solution is manganese chloride.

5. The method of claim 2, wherein said salt solution is erbium chloride.

6. The method of claim 2, wherein said salt solution is dysprosium chloride.

7. The method of claim 2, wherein said solution is terbium chloride.

8. The method of claim 2, wherein said salt solution is holmium chloride.

9. The method of claim 2, wherein said magnetic field has a gradient in a predetermined direction providing a region of most intense field strength, said salt solution being more strongly attracted by said magnetic field than is said material of interest, whereby a differential force is developed tending to push said material away from the region of most intense field strength.

10. The method of claim 9, wherein said material is diamagnetic.

11. The method of claim 9, wherein said salt solution is ferric chloride.

12. The method of claim 9, wherein said salt solution is manganese chloride.

13. The method of claim 9, including the step of adding to said solution an agent tending to suppress crystallization of the salt.

14. The method of claim 13, wherein said agent is photographic gelatin.

15. The method of claim 1, wherein said solution causes an initially non-magnetic material to become magnetic whereby said material will be drawn towards an increasing magnetic field.

16. The method of claim 15, wherein said material is given a positive susceptibility greater than that of the solution.

* * * * *

UNITED STATES PATENT OFFICE
CERTIFICATE OF CORRECTION

Patent No. 4,187,170      Dated February 5, 1980

Inventor(s) Vernon C. Westcott and John P. Bowen

It is certified that error appears in the above-identified patent and that said Letters Patent are hereby corrected as shown below:

Column 6, line 21    After "magnetic" insert --atoms--

Signed and Sealed this

Third Day of June 1980

[SEAL]

Attest:

SIDNEY A. DIAMOND

Attesting Officer    Commissioner of Patents and Trademarks